United States Patent
Matur et al.

(10) Patent No.: US 11,680,111 B2
(45) Date of Patent: *Jun. 20, 2023

(54) METHOD FOR SEPARATION OF PROTEIN AND OTHER IMPURITIES FROM MICROBIAL CAPSULAR POLYSACCHARIDES

(71) Applicant: Biological E Limited, Telangana (IN)

(72) Inventors: Ramesh Venkat Matur, Telangana (IN); Vivek Babu Kandimalla, Telangana (IN); Narender Dev Mantena, Telangana (IN); Mahima Datla, Telangana (IN); Muthyala Venkateswara Reddy, Telangana (IN); Kantam Charan, Telangana (IN)

(73) Assignee: BIOLOGICAL E LIMITED

( * ) Notice: Subject to any disclaimer, the term of this patent is extended or adjusted under 35 U.S.C. 154(b) by 96 days.

This patent is subject to a terminal disclaimer.

(21) Appl. No.: 17/035,037

(22) Filed: Sep. 28, 2020

(65) Prior Publication Data

US 2021/0017300 A1  Jan. 21, 2021

Related U.S. Application Data

(62) Division of application No. 15/568,558, filed as application No. PCT/IN2016/000107 on Apr. 25, 2016, now Pat. No. 10,836,839.

(30) Foreign Application Priority Data

Apr. 28, 2015 (IN) .......................... 2161/CHE/2015

(51) Int. Cl.
*A61K 39/09* (2006.01)
*C08B 37/00* (2006.01)
*C12P 19/04* (2006.01)
*A61K 39/00* (2006.01)

(52) U.S. Cl.
CPC ........ *C08B 37/0003* (2013.01); *A61K 39/092* (2013.01); *C12P 19/04* (2013.01); *A61K 39/00* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 4,242,501 A | 12/1980 | Cano et al. | |
| 5,714,354 A | 2/1998 | Arnold et al. | |
| 5,847,112 A | 12/1998 | Kniskern et al. | |
| 9,095,567 B2* | 8/2015 | Khandke | A61P 31/04 |
| 9,492,559 B2* | 11/2016 | Emini | A61P 31/04 |

FOREIGN PATENT DOCUMENTS

| | | |
|---|---|---|
| CN | 103623401 | 3/2014 |
| IN | 1572/MUM/2010 | 8/2012 |
| WO | WO 99/039739 | 8/1999 |
| WO | WO 2006/082527 | 8/2006 |
| WO | WO 2008/035372 | 3/2008 |
| WO | WO 2008/045852 | 4/2008 |
| WO | WO 2012/127485 | 9/2012 |

OTHER PUBLICATIONS

Anonymously Disclosed, "A Novel Purification Process for Pneumococcal Polysaccharide Antigen," ip.com Disclosure No. IPCOM000237738D (publication date: Jul. 8, 2014).
Chmelik et al., "Characterization of dextrans by size-exclusion chromatography on unmodified silica gel columns, with light-scattering detection, and capillary electrophoresis with laser-induced fluorescence detection," Journal of Chromatography 790:93-100.
International Search Report and Written Opinion dated Feb. 9, 2016 for International Application No. PCT/IN2016/000107.
Laferriere et al., "Streptococcus pneumoniae Type 14 Polysaccharide-Conjugate Vaccines: Length Stabilization of Opsonophagocytic Conformational Polysaccharide Epitopes," Infection and Immunity 2441-2446 (publication date: Jun. 1998).
Suarez et al., "Production of Capsular Polysaccharide of Streptococcus pneumoniae Type 14 and Its Purification by Affinity Chromatography," Applied and Environmental Microbiology 67(2):969-971 (publication date: Feb. 2001).

* cited by examiner

*Primary Examiner* — Jennifer E Graser
(74) *Attorney, Agent, or Firm* — Perkins Coie LLP

(57) ABSTRACT

The invention relates to a method for the removal of protein and other impurities from microbial capsular polysaccharides. More particularly, the present invention relates to isolation of microbial capsular polysaccharides in pure form after removal of protein and other impurities.

5 Claims, 3 Drawing Sheets

METHOD FOR SEPARATION OF PROTEIN AND OTHER IMPURITIES FROM MICROBIAL CAPSULAR POLYSACCHARIDES

CROSS-REFERENCE TO RELATED APPLICATION(S)

This application is a divisional of U.S. patent application Ser. No. 15/568,558, filed on Oct. 23, 2017, which is a 371 U.S. National Stage Application of International Patent Application No. PCT/IN2016/000107 filed Apr. 25, 2016, which claims priority to Indian Patent Application Serial No. 2161/CHE/2015 filed on Apr. 28, 2015, the entire contents of each of which are incorporated herein by reference and relied upon.

TECHNICAL FIELD

The invention relates to a method for the removal of protein and other impurities from microbial capsular polysaccharides. More particularly, the present invention relates to isolation of microbial capsular polysaccharides in pure form after removal of protein and other impurities.

BACKGROUND

Vaccines mimic specific disease and in doing so it makes body to elicit a defence mechanism or raise an immune response providing body to fight the pathogen. The process of manufacture of vaccine is particularly critical at every stage to determine it safe for human use. Polysaccharides are carbohydrates used in a number of industrial applications, such as thickeners, gellants, emulsifiers, and delivery systems of many commercial products. The capsular polysaccharides present on microbial cells may also be used as a component of immunization. Upon immunization with purified capsular polysaccharides in a formulated composition it prevents against disease causing organisms like *Neisseria meningitidis, Streptococcus pneumoniae, Haemophilus influenzae* type b, and *Salmonella typhi* by inducing the respective immune response.

Conjugated vaccines trigger improved immunogenic responses including in children and immune compromised individuals and also in elderly population. The polysaccharide conjugated with proteins like $CRM_{197}$, tetanus toxoid, diphtheria toxoid, other surface proteins are well proven and highly immunogenic. Pneumovax 23 is a combination of unconjugated-polysaccharide from different pneumococcal serotypes, Prevnar 13 in turn is a tridecavalent conjugated polysaccharide of 13 pneumococcal serotypes. Protein polysaccharide conjugates have been effectively used as prophylactic agents for the treatment of meningitis, bacteremia, pneumonia, epiglottitis etc.

All such immunogenic or vaccine preparations approved for human use require polysaccharides in highly purified forms. Capsular polysaccharides are present on outer surface of bacterial cell. During separation of polysaccharides from the cell there is release of cellular components like nucleic acid, proteins, cell wall etc. Process for the isolation/purification of polysaccharide involves multiple steps ranging from chromatography, filtration, treatment with detergents, solvents, enzymes to hydrolyze the nucleic acid, protein, polysaccharide etc.

In the preparation of multivalent conjugate pneumococcal vaccines directed to the prevention of invasive diseases caused by the organism *Streptococcus pneumoniae*, the selected *Streptococcus pneumoniae* serotypes are grown in an optimized nutrient to get the required polysaccharides needed to produce the vaccine. The cells are grown in large fermentors with lysis induced at the end of the fermentation by addition of sodium deoxycholate (DOC) or an alternate lysing agent. The lysate broth is then harvested for downstream purification and the recovery of the capsular polysaccharide which surrounds the bacterial cells. Although the cellular lysate produced in this process contains the target polysaccharide, it also contains large quantities of cellular debris including protein, nucleic acids cell wall components and other impurities.

The following references disclose various methods for the removal of protein and other impurities from capsular polysaccharides.

IPCOM000237738D (2014) disclosed the purification of pneumococcal polysaccharide antigens wherein a chromatographic step using Capto™ adhere, a multimodal anion exchanger, has been developed to replace the traditional hazardous step of phenol extraction.

1572 MUM/2010 discloses a purification process for removal of protein contaminants from antigenic polysaccharide which comprises: a) obtaining crude bacterial polysaccharide from lysed broth; b) subjecting the crude polysaccharide to concentration and diafiltration; c) treatment of the solution comprising polysaccharide with nuclease; d) treatment of nuclease treated polysaccharide solution with a mixture of detergent & saline; e) adjusting the pH between 6.1 and 6.3 and incubating mixture at 2 to 8° C. for 10 to 14 hrs; f subjecting the polysaccharide solution to centrifugation followed by diafiltration; g) processing the solution by chromatography, wherein said process results in reduction of protein.

U.S. Pat. No. 4,242,501 discloses a method of preparing the purified capsular polysaccharide which involves one or two alcohol precipitations.

U.S. Pat. No. 5,714,354 described an alcohol free process for the purification of pneumococcal polysaccharide using cationic detergents.

U.S. Pat. No. 5,847,112 disclosed a process for making a size-reduced capsular polysaccharide of *Streptococcus pneumoniae* of serotype 6B having decreased polydispersity which comprises decreasing the size of crude capsular polysaccharide of serotype 6B by subjecting the capsular polysaccharide to a size-reducing treatment selected from the group consisting of: thermal treatment, sonic treatment, chemical hydrolysis, endolytic enzyme treatment, and physical shear.

WO 2006/082527 A2 discloses a purification process for the capsular polysaccharide of *S. agalactiae* in which the saccharide is initially treated with an aqueous mixture of an alcohol and a calcium salt, followed by precipitation with a cationic detergent.

WO 2008/045852 A2 described a process for the purification of pneumococcal polysaccharide serotype 3 wherein heating and low pH precipitation process were employed.

WO 2012/127485 A1 discloses an alcohol and CTAB free method for the purification of pneumococcal polysaccharides which utilizes chromatographic separation of C-Ps from the polysaccharides (PnPs) on the basis of differences in their net surface charge.

However the above prior art references disclose chromatography, low pH precipitation, alcohol precipitation, alcohol free process, etc., for removal of impurities which are tedious and need multiple processing steps. Some have shown minimal reduction in impurities with subsequent difficulty in removing soluble proteins to meet purified polysaccharide specifications and therefore there is high burden of removal of contaminating soluble protein particularly for certain serotypes. Phenol is toxic and chromatography methods need more technical inputs and costly resins, which makes the process commercially not economical. Hence, there is a need for improved methods for the removal of protein impurities from complex cellular lysates.

The inventors of the present invention during their continuous efforts to develop a simple, efficient process that could be easily scaled up, found that when the solution containing polysaccharide and other impurities is exposed to $SiO_2$, the resultant solution is highly enriched polysaccharide with reduced protein and other impurities.

Objective of the Invention

It is the objective of the present invention to provide an improved process for the purification of polysaccharides with reduced protein content and other impurities and which can be easily scaled up.

Another objective of the present invention is to provide an improved process for the purification of polysaccharide in a simple and efficient manner.

SUMMARY

Accordingly, the present invention provides a method for the isolation of polysaccharide in a substantially pure form which comprises, exposing or contacting a solution comprising polysaccharide, protein, nucleic acid cell wall components and other impurities with S1O2 (silicon dioxide) and isolating the polysaccharide from a mixture of protein, nucleic acid, cell wall polysaccharide, and other cell derived materials.

DETAILED DESCRIPTION

Figure 1:
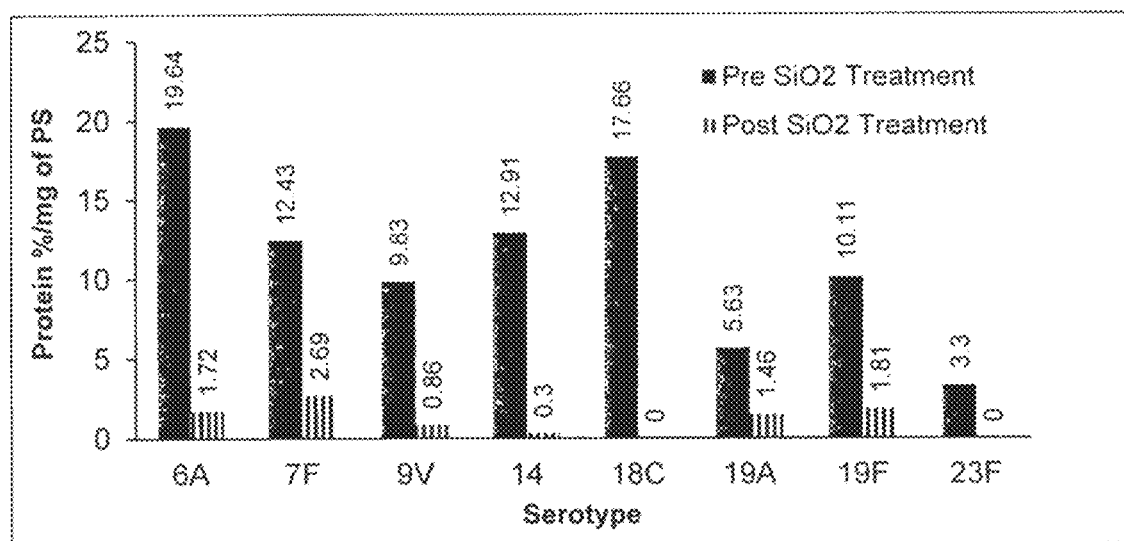
FIG. 1: Comparative protein impurity levels from different pneumococcal serotypes before and after $SiO_2$ treatment.

The present invention provides a method for the isolation of polysaccharide, wherein the source of polysaccharide is from bacteria, yeast, filamentous fungus, algae or plant cells and the like, which comprises, exposing a solution comprising polysaccharide with $SiO_2$ and optionally with other agents. The resulting solution after exposure to $SiO_2$ and separation, is enriched in polysaccharide and reduced in one or more impurities such as protein, nucleic acid, cell wall polysaccharide, and other cell derived materials.

The polysaccharides obtained according to the present invention are in substantially pure form.

In a preferred embodiment, the invention relates to methods for the reduction or removal of protein impurities from a complex cellular *Streptococcus pneumoniae* lysate or centrate comprising one or more serotypes 1, 2, 3, 4, 5, 6A, 6B, 7F, 8, 9N, 9V, 10A, 11A, 12F, 14, 15B, 17F, 18C, 19F, 19A, 20, 22F, 23F, and 33F polysaccharides.

In an embodiment, the $SiO_2$ used may be in different forms/particle size such as fine particles ranging from 0.01 µm to 200 µm, preferably in the range of 3 to 40 µm. The amount of $SiO_2$ used may range from 0.5 to 20% (w/v). $SiO_2$ used may optionally be prepared by heating above 60° C. and for at least 1 hr and cooling prior to use. The $SiO_2$ used may be pyrogenated or depyrogenated.

In yet another embodiment, other agents used for the purification process of polysaccharide may be selected from sodium chloride, ammonium sulphate and the like at a concentration of at least 0.1% (w/v) or organic solvents such as alcohol at a concentration of at least 2% (v/V). The other agent may be used to further reduce the impurities and enrich the solution with polysaccharide.

In another embodiment, the pH of the solution may be maintained in the range from acidic region to alkaline region, and preferably from 3.0 to 9.0. The pH may be adjusted using acids such as acetic acid, phosphoric, formic acid, hydrochloric acid and the like and alkalis such as sodium, potassium or ammonium hydroxide and the like.

In another embodiment, contact or exposure of the solution comprising polysaccharide and other impurities to $SiO_2$ is carried out at a temperature ranging from 15° C. to 60° C. for a period of 10 min to 16 hrs.

In another embodiment, the present invention involves treatment of polysaccharide solution with activated charcoal for removing color and other impurities. This treatment is carried out before exposure to $SiO_2$ or after exposure to $SiO_2$.

The polysaccharides purified using the method described in this invention may be used for different applications like cosmetics, food, pharma and biopharma industries.

As used herein, the term "substantially pure form" refers to a polysaccharide lysate or centrate from which at least 30% of protein has been removed compared to the concentration of protein in the lysate or centrate prior to $SiO_2$ exposure. Methods for the quantification of protein concentration in a cellular lysate or centrate are well known in the art and include, for example, biochemical methods such as Bradford assay, BCA assay, Lowry assay, analysis methods such as sodium dodecyl sulfate polyacrylamide gel electrophoresis (SDS-PAGE) analysis, chromatography, and electrophoresis (See, e.g., Deutscher, M. P. (ed.), Guide to Protein Purification, San Diego: Academic Press, Inc. (1990)).

The invention also provides a process for purifying capsular saccharide from bacteria, wherein (a) the yield of the process is at least 10% and (b) the relative purity of the saccharide is at least 30%.

In another embodiment, the present invention provides a method for the isolation of polysaccharide in a pure form which comprises,
i). exposing a solution comprising polysaccharide, protein, nucleic acids cell wall components and other impurities with $SiO_2$,
ii). isolating the polysaccharide solution in a pure form and
iii). separating the silica particles from polysaccharide by filtration or by centrifugation.

The polysaccharide concentration obtained in the process of the present invention may be from 0.1 to more than 10 mg/ml.

In another embodiment, the present invention provides a method for the isolation of polysaccharide in a pure form which comprises,
i). preparing polysaccharide solution comprising polysaccharide, protein, nucleic acids, cell wall components and other impurities, ii). treating the polysaccharide solution with detergent to remove nucleic acid and other impurities
iii). preparing a suspension of $SiO_2$ in water or a buffer,
iv). adding the suspension of $SiO_2$ to the polysaccharide solution of step (i) and iv). isolating the polysaccharide solution in a pure form.

The buffers used in the present invention for the isolation of polysaccharide includes sodium phosphate buffer, potassium phosphate buffer, tris buffer etc., Proteins are having hydrophilic surfaces and hydrophobic pockets. When polysaccharide preparations incubated with Silicon dioxide, protein impurities get bound with silicon dioxide and separated from the polysaccharide, hydrophilic or hydrophobic or simple adsorption mechanism.

The detergents used in the present invention includes CTAB (Cetyl trimethylammonium bromide), Cetrimonium chloride, Benzethonium chloride etc, The terms exposing or contacting means incubation of polysaccharide preparation with other components to treat the sample for the removal of impurities, to make pure polysaccharide.

In a preferred embodiment, the present invention provides a method for the isolation of polysaccharide in a pure form which comprises,
i) preparing polysaccharide solution comprising pneumococcal capsular polysaccharide, protein, nucleic acids cell wall components and other impurities, wherein the pH of the solution is maintained in the range of from 3.0 to 9.0.
ii) optionally adding other reagent,
iii) optionally treating the solution with activated charcoal,
iv) preparing a suspension of $SiO_2$ having particles ranging from 0.01 μm to 200 μm in water or a buffer,
v) adding the suspension of $SiO_2$ to the polysaccharide solution of step (i) at a temperature in the range of 15° C. to 60° C. for a period of 10 min to 20 hrs
vi) optionally treating the solution with activated charcoal,
vii) optionally adding other reagent and
viii) isolating the polysaccharide solution in a pure form.

The other reagents may be selected from sodium chloride, ammonium sulphate, alcohol and the like or mixture thereof.

The purified capsular polysaccharide of the invention can be used as an immunogen with or without further modification for use in immunization. For immunization purposes it is preferred to conjugate the saccharide to a carrier molecule, such as a protein.

Preferred carrier proteins are bacterial toxins or toxoids, such as diphtheria toxoid or tetanus toxoid or CRM197 mutant of diphtheria toxin etc.

In yet another embodiment, the present invention provides an immunogenic composition comprising capsular polysaccharide prepared according to the present invention conjugated to carrier protein selected from diphtheria toxoid or tetanus toxoid or CRM197.

In yet another preferred embodiment, the present invention provides an immunogenic composition comprising capsular polysaccharides from one or more serotypes 1, 2, 3, 4, 5, 6A, 6B, 7F, 8, 9N, 9V, 10A, 11A, 12F, 14, 15B, 17F, 18C, 19F, 19A, 20, 22F, 23F, and 33F conjugated to CRM197 carrier protein.

Some common brand names of $SiO_2$ (silicon dioxide) available in the market are Aerosil®, Aeroperl® may be used in the present invention.

Polysaccharide solution comprising polysaccharide, protein, nucleic acids cell wall components and other impurities can be prepared by any of the methods known the art.

The isolation of the capsular polysaccharide in pure form after exposing or contacting with $SiO_2$ is carried out by conventional methods.

The present invention is more specifically illustrated with reference to the examples given below. However, it should be understood that the present invention is not limited by an example in any manner.

Example 1

*Streptococcus pneumoniae* fermentation broth, cell lysis was carried out by adding Deoxycholate (0.005% to 2%). Post Deoxycholate incubation broth was centrifuged at 10000 to 15000 g and supernatant was collected. Supernatant pH was adjusted with acids like orthophosphoric acid, hydrochloric acid etc. to pH 4-6 and incubated for 3 hrs to overnight. Few serotypes pH was again adjusted to neutral and heated up to 60° C. for 10 to 150 min. Centrifuged the polysaccharide at 10000 to 15000 g, pellet was discarded. Further clarified the supernatant by passing through depth filter or 0.22 or 0.45 μm filter. Concentrated the filtrate 4 to 15 folds on ultrafiltration membrane 30 to 300 kDa. Concentrate was buffer exchanged up to 4 to 12 dia volumes on Phosphate buffer. To the Concentrated and buffer exchanged polysaccharide, CTAB was added, i.e. 0.2% to 5%, incubated for 2 hr to overnight at 4° C. to 40° C. Sodium chloride was added to few polysaccharides before CTAB addition in the range of 0.05M to 2M.

After CTAB treatment pellet was separated by centrifugation at 10000 to 15000 g. Supernatant was passed through charcoal column/filters. Activated silicon dioxide added to charcoal filtered polysaccharide in the range of 3 to 10% (W/V) and added NaCl from 0.5M to 3M. Polysaccharide preparation was exposed to silicon dioxide for 2 hrs to 26 hrs at temperature 5° C. to 40° C. Silicon dioxide was separated from polysaccharide solution by centrifugation/cloth filtration/bag filtration. Filtrate was passed through depth filter, carbon filter and 0.22 to 5μm filter. Filtered Polysaccharide was concentrated and diafiltered on 10 kDa to 500 kDa membrane. Polysaccharide was buffed exchanged into phosphate buffer or WFI. Purified polysaccharide preparation was passed through 0.22 μm filter and collected into LDPE bag under LAFU. The purified polysaccharide was stored at >−20° C.

TABLE 1

Protein removal from different Pneumo polysaccharides

| | Serotype | | | | | | | |
|---|---|---|---|---|---|---|---|---|
| | Pneumococcal Serotype 1 | | Pneumococcal Serotype 6A | | Pneumococcal Serotype 7F | | Pneumococcal Serotype 19A | |
| | Pre Treatment | Post Treatment | Pre Treatment | Post Treatment | Pre Treatment | Post Treatment | Pre Treatment | Post Treatment |
| Polysaccharide (mg/mL) | 1.9 | 1.77 | 2.82 | 2.62 | 3.6 | 2.72 | 2.67 | 2.5 |
| Protein (mg/mL) | 0.34 | BDL | 0.26 | BDL | 0.26 | 0.05 | 0.59 | BDL |
| Protein % (per mg of PS) | 17.89 | BDL | 9.22 | BDL | 7.22 | 1.84 | 22.10 | BDL |

BDL: Below detection limit

This embodiment describes the influence of depyrogenation on impurity removal from the polysaccharide preparation. As depicted in Table 2 protein impurity was removed by both depyrogenated and pyrogenated $SiO_2$. Hence depyrogenated as well as pyrogenated $SiO_2$ can be used for the removal of impurities.

TABLE 2

Influence of aeroeprl ® depyrogenation on protein removal from different pneumococcal polysaccharides.

| Pneumococcal Serotype 6B | Description | Pre treatment | Post treatment |
|---|---|---|---|
| Pyrogenated $SiO_2$ | Protein (mg/mL) | 0.21 | BDL |
| | Protein % (per mg of PS) | 9.86 | BDL |
| | Polysaccharide (mg/mL) | 2.13 | 1.27 |
| Depyrogenated $SiO_2$ | Protein (mg/mL) | 0.23 | BDL |
| | Protein % (per mg of PS) | 8.07 | BDL |
| | Polysaccharide (mg/mL) | 2.85 | 1.5 |

BDL: Below detection limit

Conditions: Aeroperl® 5% (w/v), NaCl 1M, Incubated at room temperature for 1h.

Aerosil® can be used in a range from 0.1% to 10% or higher concentration. Protein was completely removed by treatment with $SiO_2$ in an hour to more than 17 hrs. Impurity removal can be improved by the addition of NaCl to the $SiO_2$ suspension.

TABLE 3

Influence of Aerosil ® concentration on Protein removal from Pneumococcal polysaccharide serotype 6B

| S. No. | Parameter | Pre-Aeroperl treatment | Post 2% Aeroperl treatment | Post 3% Aeroperl treatment | Post 4% Aeroperl treatment | Post 5% Aeroperl treatment |
|---|---|---|---|---|---|---|
| 1 | Protein (mg/ml) | 0.23 | BDL | BDL | BDL | BDL |
| 2 | Protein % (per mg of PS.) | 8.07 | BDL | BDL | BDL | BDL |
| 3 | PS (mg/ml) | 2.85 | 1.68 | 1.62 | 1.52 | 1.49 |

BDL: Below detection limit
Conditions: NaCl 1M; Incubated at room temperature for 1h.

This embodiment also supports that depyrogenated Aeroeprl® can remove the protein effectively in presence of NaCl ranging from 0.1M to 2.5M or above. $SiO_2$ particles can be used in the range or size from 0.1 μm to 100 s of microns.

TABLE 4

Influence of aeroperl concentration on protein removal from pneumococcal polysaccharide, serotype 6B

| S. No. | Parameter | Pre-Aeroperl treatment | Post 2% Aeroperl treatment | Post 3% Aeroperl treatment | Post 4% Aeroperl treatment | Post 5% Aeroperl treatment |
|---|---|---|---|---|---|---|
| 1 | Protein (mg/ml) | 0.23 | BDL | BDL | BDL | BDL |

TABLE 4-continued

Influence of aeroperl concentration on protein removal from pneumococcal polysaccharide, serotype 6B

| S. No. | Parameter | Pre-Aeroperl treatment | Post 2% Aeroperl treatment | Post 3% Aeroperl treatment | Post 4% Aeroperl treatment | Post 5% Aeroperl treatment |
|---|---|---|---|---|---|---|
| 2 | Protein % (per mg of PS.) | 8.07 | BDL | BDL | BDL | BDL |
| 3 | PS (mg/ml) | 2.85 | 1.68 | 1.62 | 1.52 | 1.49 |

BDL: Below detection limit
Condition: NaCl 1M, Incubated at room temperature for 1h Fermentation broth contains number of contaminants. These contaminants can be removed in series of steps like centrifugation, precipitation, chromatography etc.

Current invention was carried at small scale (50-100 ml) and pilot (15 L) level. At both volumes of polysaccharide, contaminants were efficiently removed by the different forms of $SiO_2$ (Table 5 and FIG. 1). $SiO_2$ treatment can be introduced at different stages of the' polysaccharide purification. Further $SiO_2$ particles can be separated by simple centrifugation or filtration or by any other method such as physical settling, pressure settling etc.

TABLE 5

Protein impurities diminution using aeroperl from Pneumococcal polysaccharides

| | Serotype | | | |
|---|---|---|---|---|
| | Pneumo Serotype 1 | | Pneumo Serotype 6B | |
| | | condition | | |
| Parameter | Pre Aeroperl treatment | Post Aeroperl treatment | Pre Aeroperl treatment | Post Aeroperl treatment |
| Protein (mg/mL) | 0.21 | BDL | 0.23 | BDL |
| Protein % (per mg of PS) | 9.86 | BDL | 8.07 | BDL |
| Polysaccharide (mg/mL) | 2.13 | 1.88 | 2.85 | 1.52 |

BDL: Below detection limit.
Conditions: Aeroperl: 5% (w/v), NaCl 1M, Incubated at room temperature for 1h

TABLE 6A

Protein impurity removal from capsular polysaccharide of different pneumococcal serotypes

| | Serotype | | | | | | | |
|---|---|---|---|---|---|---|---|---|
| | Pneumococcal Serotype 6A | | Pneumococcal Serotype 7F | | Pneumococcal Serotype 9V | | Pneumococcal Serotype 14 | |
| | | | | Condition | | | | |
| Parameter | Pre | Post | Pre | Post | Pre | Post | Pre | Post |
| Protein (mg/mL) | 0.88 | 0.14 | 1.15 | 0.21 | 0.86 | 0.07 | 0.67 | 0.01 |
| Protein % (per mg of PS) | 9.64 | 1.72 | 12.43 | 2.69 | 9.83 | 0.86 | 12.91 | 0.30 |
| Polysaccharide (mg/mL) | 9.13 | 8.15 | 9.25 | 7.81 | 8.75 | 8.11 | 5.19 | 3.38 |

Pre: Pre aeroperl treatment; Post: Post aeroperl treatment
Condition: Aeroperl 5% (w/v), NaCl 1M, Incubated at room temperature for 1h.

TABLE 6B

Protein impurity removal from capsular polysaccharide of different Pneumococcal polysaccharide serotypes

| | Serotype | | | | | | | |
|---|---|---|---|---|---|---|---|---|
| | Pneumococcal Serotype 18C | | Pneumococcal Serotype 19A | | Pneumococcal Serotype 19F | | Pneumococcal Serotype 23F | |
| | | | condition | | | | | |
| Parameter | Pre | Post | Pre | Post | Pre | Post | Pre | Post |
| Protein (mg/mL) | 0.89 | BDL | 0.48 | 0.1 | 0.67 | 0.11 | 0.1 | BDL |
| Protein % (per mg of PS) | 17.66 | BDL | 5.63 | 1.46 | 10.11 | 1.81 | 3.30 | BDL |
| Polysaccharide (mg/mL) | 5.04 | 4.48 | 8.52 | 6.85 | 6.63 | 6.09 | 3.03 | 2.51 |

BDL: Below detection limit
Pre: Pre aeroperl treatment; Post: Post aeroperl treatment
ND: Not detected
Condition: Aeroperl 5% (w/v), NaCl 1M, Incubated at room temperature for 1h Limit of contaminants have been set for the purified polysaccharide of each serotype to reduce the risk of adverse events from the vaccine. Among contaminants CWPS is one. Current invention has been taken care of CWPS. CWPS was removed at room temperature by simple mixing and followed by separation of S1O2 from the polysaccharide sample. Polysaccharide sample with $SiO_2$ contact time may vary from 10 min to more than 18 hrs (Table 7).

TABLE 7

Removal of cell wall polysaccharide (CWPS) from different serotypes of pneumococcal polysaccharides

| | Serotype | | | |
|---|---|---|---|---|
| | Pneumo Serotype 19A | | Pneumo Serotype 19F | |
| | Condition | | | |
| Parameter | Pre Aerosil treatment | Post Aerosil treatment | Pre Aerosil treatment | Post Aerosil treatment |
| CWPS (mg/ml) | 0.484 | 0.031 | 0.108 | 0.038 |
| CWOP %(per mg of PS) | 12.94 | 1.40 | 3.45 | 1.65 |
| Polysaccharide (mg/mL) | 3.74 | 2.22 | 3.13 | 2.3 |

Conditions: Aerosil 5% (w/v), NaCl 1M; Incubated at room temperature for 1h

Protein impurity removal can be visualised by SDS-PAGE. Pneumococcal polysaccharide serotype 18C and 23F protein impurity was reduced to limit of specification. As depicted in the FIGS. 2 and 3, clear removal of protein can be seen in lane 2 and 3. Results were represented in table 8.

TABLE 8

Figure 2:
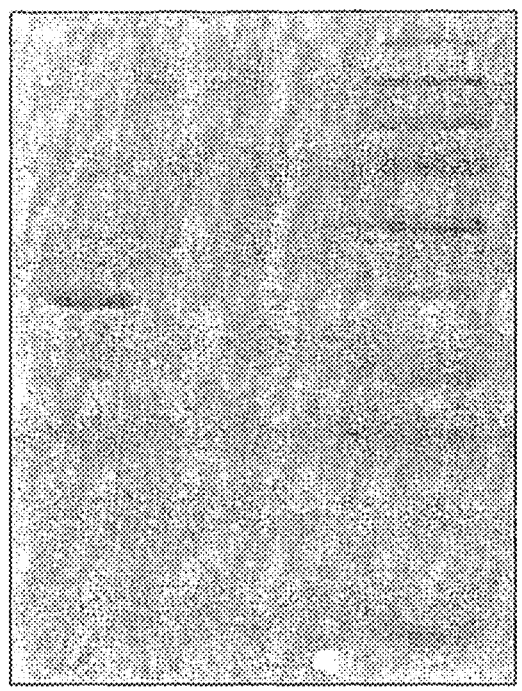
FIG. 2: SDS-PAGE results for pneumococcal polysaccharide serotype 18C; protein reduction before and after $SiO_2$ treatment.
Figure 3:
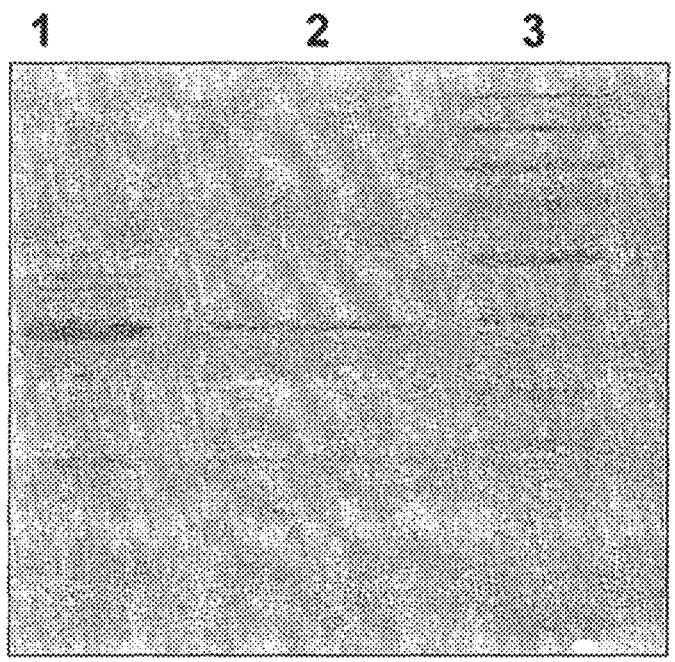
FIG. 3: SDS-PAGE results for pneumococcal polysaccharide serotype 23F; protein reduction before and after $SiO_2$ treatment.

Protein concentration before and after aeroperl ® treatment (FIG. 2 and 3)

| Pnumococcal Polysaccharide Serotype | Before aeroperl ® treatment | | | After aeroperl ® treatment | | |
|---|---|---|---|---|---|---|
| | PS mg/ml | Protein mg/ml | Protein %/ mg of PS | PS mg/ml | Protein mg/ml | Protein %/ mg of PS |
| 23F | 3.03 | 0.1 | 3.30 | 2.4 | BDL | BDL |
| 18C | 4.49 | 0.33 | 7.35 | 4.79 | 0.02 | 0.42 |

We claim:

1. A method for preparing an immunogenic composition comprising a purified capsular polysaccharide conjugated to a carrier protein selected from the group consisting of diphtheria toxoid, tetanus toxoid, and $CRM_{197}$, the method comprising:

exposing or contacting a solution of lysed *Streptococcus pneumoniae* cells comprising the capsular polysaccharide, proteins, nucleic acids, cell wall components and other impurities with silicone dioxide ($SiO_2$);

separating the capsular polysaccharide from the $SiO_2$ by filtration or by centrifugation and without using chromatography to isolate the capsular polysaccharide in substantially pure form; and conjugating the purified capsular polysaccharide to the carrier protein.

2. The method of claim 1, wherein the *Streptococcus pneumoniae* comprises one or more serotypes selected from the group comprising of 1, 2, 3, 4, 5, 6A, 6B, 7F, 8, 9N, 9V, 10A, 11A, 12F, 14, 15B, 17F, 18C, 19F, 19A, 20, 22F, 23F, and 33F.

3. The method of claim 1, wherein the $SiO_2$ comprises particles each having a size ranging from 0.01 μm to 200 μm.

4. The method of claim 1, wherein the solution of lysed cells is exposed or contacted with the $SiO_2$ at a temperature ranging from 15° C. to 60° C. for a period of time ranging from 10 minutes to 16 hours.

5. The method of claim 1, wherein the $SiO_2$ is in an amount ranging from 0.5% to 20% weight/volume (w/v).

* * * * *